United States Patent [19]

Renirie et al.

[11] 4,388,929
[45] Jun. 21, 1983

[54] PROGRAMMABLE PACER AND METHOD OF EXTERNAL PROGRAMMING

[75] Inventors: Alexis C. M. Renirie, Wijchen; Kornelis A. Mensink; Frederik H. M. Wittkampf, both of Brummen, all of Netherlands

[73] Assignee: Vitafin N.V., Curacao, Netherlands Antilles

[21] Appl. No.: 215,559

[22] Filed: Dec. 11, 1980

[51] Int. Cl.³ .............................................. A61N 1/36
[52] U.S. Cl. .............................................. 128/419 PG
[58] Field of Search ....... 128/419 PG, 420 R, 419 PT

[56] References Cited

U.S. PATENT DOCUMENTS 3,835,833  9/1974  Limoge ........................... 128/420 R
4,240,031  11/1978  Mensink et al. ............. 128/419 PG
4,245,641  2/1979  Mann et al. ................... 128/419 PG Primary Examiner—William E. Kamm Attorney, Agent, or Firm—Woodcock, Washburn, Kurtz, Mackiewicz & Norris

[57] ABSTRACT

A pacing system and method of programming the rate of said system is disclosed, wherein the pacemaker comprises circuitry for receiving a first group of simple on-off magnetic pulses which are accumulated and translated into the decades portion of the desired heartbeat rate (in bpm), and also for receiving a second group of pulses which are translated into the units count of the desired pacing rate in bpm. The circuitry provides that an initial portion of the programming signal is inspected relative to predetermined criteria, so that such initial portion acts also as an enabling key for accepting the overall programming signal. The doctor simply applies a simple hand held magnet t times according to the desired tens component of the programmed rate in bpm, maintains the magnet applied for at least a predetermined number of pacer intervals, and then applies the magnet u times corresponding to the units component of the desired heart rate, thereby programming the pacer to operate at tu bpm.

18 Claims, 3 Drawing Figures

PROGRAMMABLE PACER AND METHOD OF EXTERNAL PROGRAMMING

BACKGROUND OF THE INVENTION

This invention relates to pacemaker apparatus and a method for programming a pacemaker and in particular an apparatus and method of direct decimal programming of pacemaker rate.

The desirability of programmable pacemakers has become a clinical and commercial reality, and is well documented in the literature. There are a number of reasons why it is advantageous to be able, at any time after implantation, to change operating parameters of the pacer so as to provide more optimum operation in response to the observed condition of the patient. Presently available pacemakers provide for programming of a large number of different pacer parameters, in different combinations. However, the pacer parameter, or variable which is most widely programmed for patient treatment is that of pacing rate, i.e., the rate of delivering stimulus beats from the pacemaker to the patient's heart.

Reference is made to U.S. Pat. No. 4,124,031, issued Nov. 7, 1978, PROGRAMMABLE PACER, assigned to the same assignee. In this patent, at columns 1 and 2, there is presented a discussion concerning the desirability of having a pacing system which utilizes the most simple and reliable programming means available, namely a simple magnet. As stated in the referenced patent, an implanted pacemaker which is programmable with a simple magnet provides the patient with the most in inherently reliable means of communicating with the pacemaker, due to the virtual universal availability of simple magnets. Also, as disclosed in the referenced patent, such a pacing system programmable with a simple magnet may be made as secure as any more complex pacer in terms of avoidance of unwanted interference or spurious signals.

Having achieved the optimum system for programming the pacemaker in terms of overall lifetime reliability, a next design objective becomes that of providing a technique, or method of programming which is inherently simple for the physician to utilize, and which also can be performed very quickly. Many present day programmable pacer models require the use of a complex transmitter in order to properly program the pacemaker. Although such transmitters enable effective "pushbutton" programming, which has a certain gadget appeal, it is necessary for the physician to properly initialize the programmer/transmitter by ensuring that it has power, setting the dials properly, positioning it accurately, etc. Even then, having thrown the proper switch or pushed the proper button, the physician has no feel or sense that the programming has been achieved properly, and must follow the standard test procedures to determine that indeed the desired program has been received.

By contrast with the more complex programming arrangements, the essence of the subject invention is to provide a simple programming arrangement to which the physician can readily relate, for programming the pacemaker rate. What is provided is a simple programming code which permits the doctor to directly program and count the programmed rate as it is being entered, so that the doctor has a sense of direct control over the procedure. The pacemaker and method of this invention employs direct decimal programming, meaning that the doctor first directly enters a program signal corresponding to the decade count of the desired heart rate, and then enters a program corresponding to the units count of the heart rate. For both the decade and units programming steps, the doctor simply places the magnet over the patient's chest in the vicinity of the pacemaker and removes it a number of times corresponding to the decade and/or units count desired. By way of example, if a doctor desires to program a new rate of 75 beats per minute, he first applies the magnet (i.e., positions it in the vicinity of the patient's pacemaker so that the magnetic field thus created can be sensed within the pacemaker) and then removes it 7 times, corresponding to 7 decades or 70 beats per minute. The doctor then holds the magnet in an applied position for a predetermined minimum period, and then repeats the procedure, applying the magnet and removing it 5 times in order to introduce the desired units count. The pacemaker thereafter automatically adjusts the pacing rate according to the two inputs, providing a rate in this example of 75 bpm.

It is immediately seen that this technique of direct decimal programming is simple and easily understood, and is one which enables the physician to directly count the programmed rate as he is entering it. The "program language" that is employed is a universal language, since the decimal system is utilized universally. All physicians who deal with pacing in whatever geographical location, count heart rate in terms of bpm as expressed in decimal terms. Accordingly, the most natural and direct way of programming this parameter is to first introduce the decades, or tens count, and then introduce the units count. It is thus seen that the technique of direct decimal programming employs a natural language which the doctor immediately grasps, and which importantly provides the doctor with a means of having a sense of control over the process of programming the pacer rate. The programming method is direct, i.e., the doctor puts the program directly into the pacemaker without any intervening mechanism; it is also quick, simple and reliable.

SUMMARY OF THE INVENTION

It is an object of this invention to provide a cardiac pacemaker having means for receiving programming signals, which programming means are simple and avoid a complex design for receiving programming signals transmitted from an external source. The pacemaker design enables the programmer to program the pacemaker with simple on-off magnetic signals generated by a hand held magnet.

It is another object of this invention to provide a programmable pacing system which is adapted to be securely used in connection with a simple magnet, which system enables the programmer to program pacing rate first in decades and then in units.

It is another object of this invention to provide a pacing system and method of programming of same which utilizes direct decimal programming.

It is another object of this invention to provide a programmable pacer which utilizes a programming technique which incorporates the basic pacer timing as a reference for making program changes and for ensuring that the proper program has been entered.

It is another object of this invention to provide a programmable pacing system with simple receiving means which avoids the need for complex addressing arrangements; the pacing system provides for first entering a key in accordance with a predetermined program, to ensure security of receiving only a desired program signal.

It is a further object of this invention to provide a programmable pacer adapted to receive externally transmitted magnetic signals, and which operates in a way so as to eliminate the possibility that the programming operation might interfere with ongoing pacemaker operation.

It is another object of this invention to provide a method of direct decimal programming of the heartbeat rate in an implanted pacemaker, and to inhibit the programming of a heartbeat rate outside of a predetermined range defined by low and high rate limits.

In view of the above objects, there is provided a cardiac pacing system comprising an implantable pacemaker adapted to receive program signals, the program signals being delivered directly by the doctor and in decimal sequence, i.e., a first series of signals has a count corresponding to the decade count of the desired heartbeat rate, and is followed by a second group of signals having a count corresponding to the units count of the desired heartbeat rate. The direct decimal method of programming may be adapted to pacing systems designed to receive any variety of external programming signals, high or low frequency, electromagnetic or simple magnetic. While the preferred embodiment is specifically disclosed, equivalent circuit means of receiving a first group; of signals representing the tens, and a second group of signals representing the ones, are within the scope of the invention.

DETAILED DESCRIPTION OF THE PREFERRED EMBODIMENTS

The disclosure that follows relates to an improvement to an implantable pacemaker. It is understood that the pacemaker includes a housing, a power source, conventional circuitry, etc. Such conventional components are not shown, but are incorporated as being known and available in the art.

Figure 1:
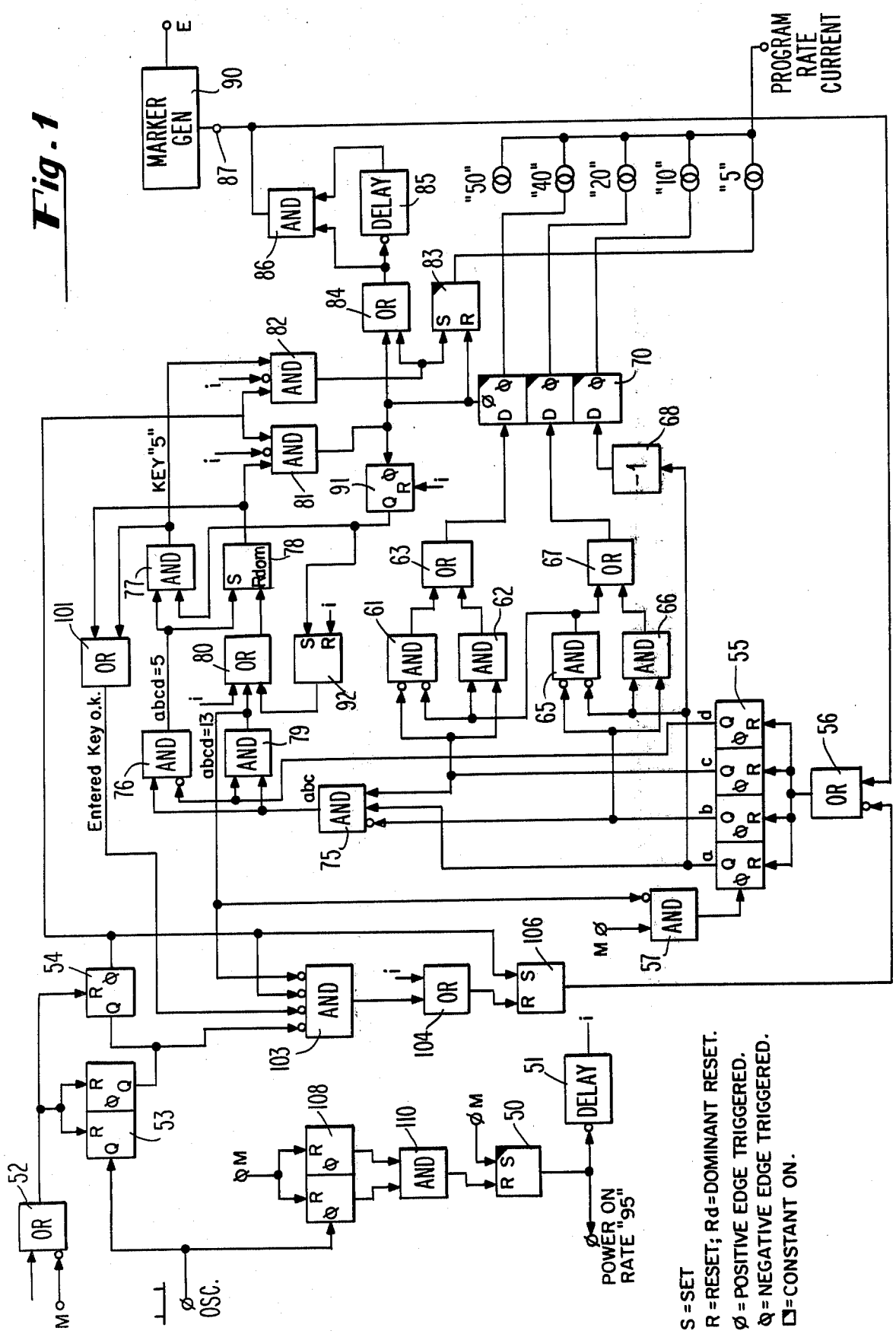
FIG. 1 is a block diagram showing the logic circuitry of the pacemaker of this invention, which logic circuitry provides for receipt of the program signals and for controlling the stimulus rate as a function of the received program signals.

Referring now to FIG. 1, there is shown a detailed block diagram of the program decoding and logic circuitry as found in the preferred embodiment of the pacemaker of this invention. As an overview, the magnet pulses (M) are received through a reed switch network or equivalent, and are gated through gate 57 into serial input shift register 55, which constitutes a counter for counting groups of input pulses. When a program sequence has been properly inputted, the contents of register 55 are decoded through gates 61–63 and 65–68 and inputted into parallel input register 70. The contents of register 70 control the operation of the rate program current generators which are designated as "5", "10", "20", and "40". The current generator designated "50" is continuously energized, corresponding to a minimum pacemaker rate of 50 bpm. Thus, for the circuit illustrated, corresponding to the inputted program signal, the rate may be controlled to any 5 bpm increment between 50 and 125. Note that there is no capability of inadvertently programming the rate below 50, nor is there any capability or possibility of programming the rate greater than 125. As seen further below, provision is made for the case where the physician may inadvertently try to program a rate outside of these limits. The remaining portion of the circuitry illustrated in FIG. 1 provides for the functions of initializing the circuitry at the start of programming, processing the inputted magnetic signal to detect the presence of "keys", when the end of a group of magnet pulses is indicated, and determining whether the magnet pulses conform to the required timing constraints.

Figure 3:
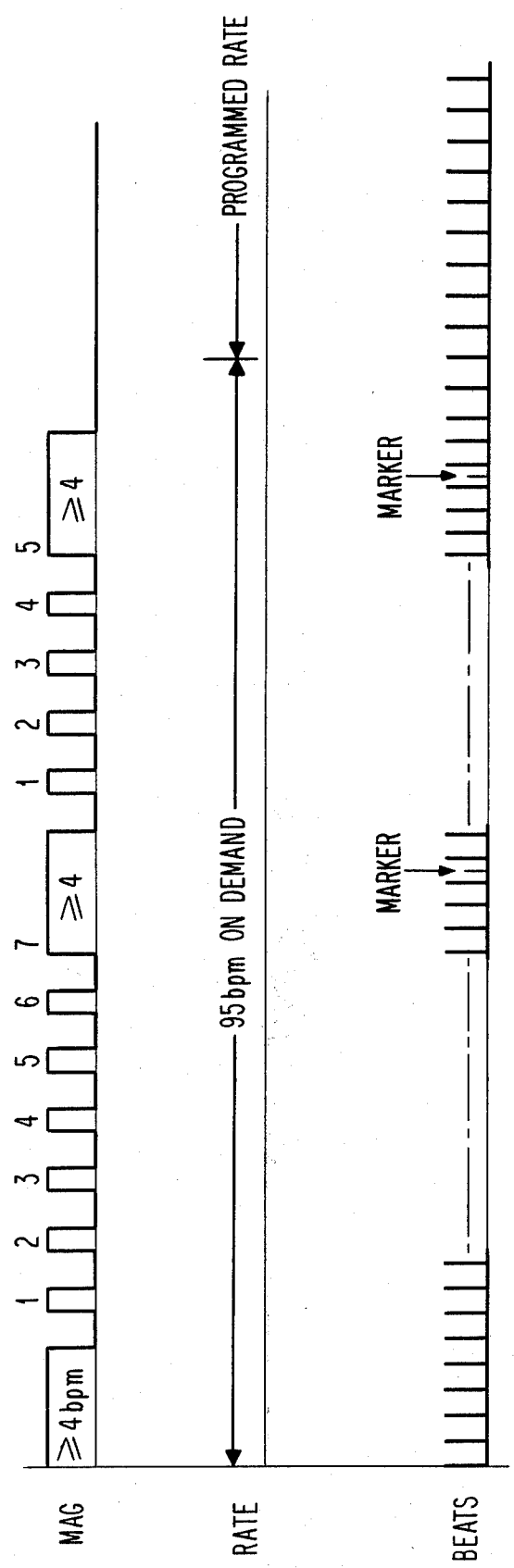
FIG. 3 is a series of graphs showing the time relationships of the external programming signal, the timing of the pacemaker stimulus generator, and the variation in pacemaker rate during and after programming.

Reference is made to the first graph of FIG. 3, which illustrates the coding of a magnet programming signal which is accepted by the system of this invention. For the embodiment as illustrated in FIG. 1, the magnet must be applied for a time period corresponding to more than 4 timing signals received from the pacer pulse generator. See referenced U.S. Pat. No. 4,124,031, for a discussion of the technique of comparing the time relationship of the program signal to the output pulses of the pacemaker stimulus generator. As is discussed below, when the magnet is applied and the M signal goes high, the pacer rate is automatically switched to 95 bpm in an on demand condition. When and as the magnet is held applied for more than 4 cycles of the 95 bpm output, the circuit is made ready to receive the first group of pulses, corresponding to the decades (tens) count. In order to enter a magnet signal into the pacemaker, the magnet must be held off for less than 3 counts and then on for less than 2 counts. As long as these constraints are met each positive magnet signal is counted in register 55. For the illustration of FIG. 3, where the physician desires to program a rate of 75, 7 such magnet pulses are applied, and then the magnet is held applied for more than 4 beats. This latter condition is sensed, whereupon the circuitry causes the count in register 55 to be decoded and transferred to register 70, for controlling the program rate current to a value corresponding to 70 bpm. If, at this point, the physician simply put the magnet away, the pacer would continue to operate at 70 bpm. However, if he follows with another 5 pulses, then the 5 count in register 55 is decoded and caused to energize the "5" current generator, such that the total program rate current causes the pacemaker stimulus generator to deliver pulses at a rate of 70 plus 5, or 75 bpm. Upon removing the magnet for more than 3 pulses, power is turned off and the programming sequence is over.

Referring again to FIG. 1, when the magnet is first applied, the positive going signal inputted to the set terminal of flip-flop 50 produces an output which is connected to turn power on to the program logic circuitry, and also to place the pacer at a rate of 95 bpm on demand (see the second graph of FIG. 3). As soon as power is turned on, the output of delay circuit 51 is high, providing an initializing signal (i) which is connected to circuits 52, 81, 82, 91, 92, and 104. However, after a predetermined short delay established by circuit 51, the inverted signal causes the output of circuit 51 to go low. Thus, the initializing signal is high for a short period, during which time initialization of necessary circuits is achieved, and thereafter the initializing signal goes low. For the remainder of the program sequence, the initializing signal has no effect on circut performance.

Register 53, a two stage series shift register, receives input timing pulses from the pacemaker oscillator. OR gate 52 has the magnet signal inputted through an inverter terminal, such that there is an output whenever the magnet signal is low, and the output goes low whenever the magnet signal is high. Since the output of OR gate 52 is connected to the reset terminals of register 53, this register is held reset whenever the magnet signal is low (off), and is allowed to count input signals whenever the magnet signal is on. The output of OR gate 52 is also connected to the reset terminal of flip-flop 54, such that it is enabled whenever the magnet signal is on. Since flip-flop 54 is negative edge triggered, it is set only every fourth oscillator pulse, when the second stage of register 53 is switched from a high to a low state. Thus, flip-flop 54 provides an output whenever the signal has been high for four oscillator pulses.

Register 108 is the "magnet off" counter, and counts oscillator timing pulses whenever the magnet signal is not present, i.e., off. The magnet signal is connected to the reset terminals of each stage, such that counter 108 is free to count only when the magnet signal is in the off condition. The output of each stage of counter 108 is connected through AND gate 110, the output of which is connected to the reset terminal of power on flip-flop 50. Thus, whenever register 108 counts to 3, indicating a magnet off signal having a time duration of 3 oscillator timing pulses, flip-flop 50 is reset, which turns off power. As a result, if the magnet is reapplied, the initializing signal i is again generated, and the program logic is initialized.

In operation, the magnet signals are gated through normally enabled AND gate 57 to the input of register 55. Register 55 is a 4 stage binary counter, having the capacity to count up to 15. Outputs from the 4 stages, designated a, b, c and d, are connected through basically 2 separate logic paths. The first path comprises gates 61–63 and 65–68, which set of gates translates the stored binary signal in register 55 into a binary signal which, when shifted into register 70, enables the proper combination of program rate current sources. Note that since the "50" current source is continuously energized, the desired binary control signal in register 70 is the actual programmed rate minus 50. The logic circuitry is thus required to perform the operation of subtracting 5 in transferring the signal from register 55 to register 70. For reasons discussed below, when the count in register 55 is less than 5 or more than 12, corresponding to rates of 40 or less and 130 or more, no binary word gets shifted into register 70. Accordingly, the logic circuitry needs to operate only upon counts 5–12 inclusive. These counts can all be determined logically from the first 3 stages, i.e, the 3 least significant bits, such that it is not necessary to make a connection from the d stage of register 55 to the decoding logic.

The second basic path which operates on the output of register 55 comprises blocks 75–87 and 90–92. Outputs from stages a, b and c of register 55 are connected to AND gate 75, the b output being connected into an inverter terminal. Thus, AND gate 75 produces a high output when and only when abc represents a count of 5. The output of gate 75 is connected as a first input to each of AND gates 76 and 79. The output of stage d of register 55 is connected as a second input to AND gate 79, and is connected to the input inverter terminal of AND gate 76. Thus, AND gate 76 provides a high output only when the d stage of register 55 is low, corresponding to register 55 holding a count of 5, i.e., abcd=5. The output of gate 76 is connected as a first input to normally disabled AND gate 77, and is connected to the set terminal of flip-flop 78. Thus, when register 55 has counted up to 5, corresponding to the doctor applying the magnet 5 times, flip-flop 78 is set, producing a high signal at its output. The output of gate 78 is connected to a first input of AND gate 81, as well as to OR gate 101. The presence of a 5 count in register 55 thus provides a signal which indicates that the key "5" has been entered, enabling AND gate 81 and also disabling AND gate 103 (due to the high signal from OR gate 101 to an inverter terminal of AND gate 103).

As seen, AND gate 81 produces a high output signal only when there is a high output from flip-flop 54, which corresponds to the magnet being held on for 4 timing pulses. This occurs only when the doctor has finished inserting the full count to register 55, following which the magnet is held applied for more than 4 counts (see FIG. 3). For example, if the doctor is programming a rate of 75, the first step constitutes applying the magnet 7 times, such that register 55 contains a 7 and flip-flop 78 remains set. The doctor then holds the magnet applied for more than 4 timing pulses, thereby producing a high output from flip-flop 54 and from AND gate 81. This latter output is connected to the positive edge triggered shift terminal of register 70, such that the count then in register 55 is decoded and transferred into register 70. For the example given, a binary 2 is shifted into register 70, thereby enabling the "20" current source (which is added to the constant "50" source). At the same time, the signal from AND gate 81 is gated through OR gate 84 to delay circuit 85 and AND gate 86. Due to the inverter input terminal of delay circuit 85, the output of AND gate 86 goes negative after the predetermined delay introduced in circuit 85. The output from AND gate 86 is connected to marker generator 90, which produces a marker generator pulse which is initiated at the trailing edge of the signal from gate 86, such that it is initiated at a predetermined delay following the pacemaker timing signal which triggered the shifting of program data into register 70. This ensures that the marker generator is positioned in a desirable time relationship with the delivered stimulus pulses. Also, the output from gate 86, which appears at node 87, is fed back through OR gate 56 to reset register 55, so that the pacemaker is ready to receive the programming of the units portion of the rate, if any.

At this point, after the doctor has programmed the decades as desired, register 55 is cleared, and the upper logic path is primed to receive the "5" count. Note that when the doctor withdraws the magnet which had been held applied for more than 4 beats, the trailing edge of the signal from AND gate 81 goes negative, triggering flip-flop 91. The output of flip-flop 91 goes high, and remains high until reset by an initializing signal, thereby enabling AND gate 77. The output of flip-flop 91 is also connected to the set terminal of flip-flop 92, causing it to produce a high output signal which is gated through OR gate 80 and resets flip-flop 78. As long as flip-flop 91 is set, a reset signal remains on flip-flop 78, holding it reset since its reset terminal is dominant. This disables any output from AND gate 81, thereby disabling shifting of new data into register 70.

Reviewing the operation whereby the units are programmed, the doctor starts to apply the magnet, whereupon register 55 counts. Nothing happens until stages abcd hold a binary 5, at which time there is a high output from gate 76, which is passed through enabled gate 77, the output of which is connected to gate 82. If the doctor stops at this point and holds the magnet applied for 4 timing pulses, a positive signal is received from flip-flop 54, producing an output from gate 82, thereby setting flip-flop 83 and turning on the "5" current generator. At the same time, a signal is inputted to OR gate 84, and a marker pulse is generated by generator 90 in the same manner as following the programming of the decades. Likewise, a signal if fed back to OR gate 56, resetting register 55. Note that if the doctor applies one or more additional magnet pulses, the output from AND gate 77 goes low, such that when the magnet is held on for 4 or more oscillator pulses nothing passes and no signal is produced to set flip-flop 83.

If, in attempting to program the pacer, the doctor applies the magnet less than 5 times or more than 13 times, no change occurs in the programmed rate. As has been seen above, for a count of 4 or less in register 55, there is no output from gate 76, and consequently flip-flop 78 does not get set, meaning that gate 81 is not enabled and there can be no change in the contents of register 70. If the doctor applies the magnet a 13th time, both input terminals to AND gate 79 are high, producing an output which passes through gate 80 and resets flip-flop 78, thus disabling gate 81. The "13" output from gate 79 is also connected to the inverter terminal of AND gate 57, which disables this gate and prevents succeeding magnet pulses from being inputted to register 55. Thus, register 55 holds at a count of 13, and when and if the doctor holds the magnet applied for more than 4 oscillator pulses, nothing is gated through gate 81 because flip-flop 78 remains reset. Thereafter when the magnet is removed, the circuitry is reinitialized, and the prior programming data remains in register 70.

Attention is drawn to the feedback path through AND gate 103, which provides for resetting of register 55 when the magnet is applied for more than 2 oscillator timing intervals. Notice that the normal constraint on entering the magnet pulses is that the magnet high signal must be less than 2 oscillator intervals, while the magnet off must be less than 3. However, another condition imposed by the programming code as illustrated is that the entered count is shifted to register 70 only by applying the magnet for more than 4 beats. These two competing conditions are accommodated by the path through gates 103 and 104 and flip-flop 106. When the second stage of register 53 goes high, the signal is passed through the gate only if the other 3 signals which are inputted through the inverter terminals remain low. It is seen that if the key "5" is entered, or abcd = 13, the AND gate is disabled. Consequently, once the key 5 has been entered, a high output from register 53 does not pass through gate 103. This permits the application of the magnet for 4 oscillator pulses, whereupon register 55 is not reset while the magnet is held applied.

There is thus illustrated logic circuitry for accepting direct decimal programming with a hand held externally applied magnet, whereby the doctor applies the magnet first for a series of pulses counting up to the desired decade count, and then applies it 5 more times if it is desired to add 5 bpm to the total. While a simplified version is illustrated wherein only "5" can be added after the decade count has been entered, it is readily understood that the pacemaker of this invention may accommodate programming of any unit value. For example, AND gate 76 is connected to decode the presence of a binary "5". If it is desired to decode any other unit, similar logic circuitry may be implemented to decode the corresponding "units" count, whereupon a selected configuration of current generators is enabled to produce the desired "units" current, which combines with the "tens" current. Just as the output of flip-flop 91 enables AND gate 77, the output of flip-flop 91 may enable 9 different gates which in turn would decode any one of 9 different counts inputted into register 55, corresponding to unit values of 1–9. Of course, the theory of the invention can be extrapolated to program "hundreds" separately, as well as "tenths".

Figure 2:
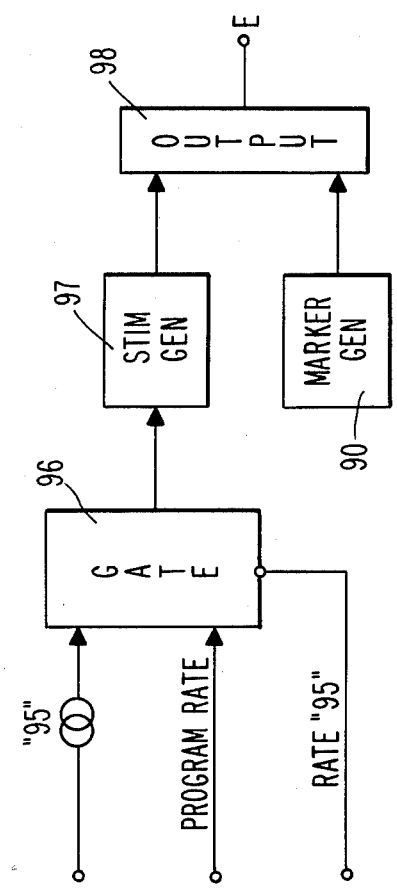
FIG. 2 is a simple block diagram illustrating control of the output as a function of the received program signal.

Referring now to FIG. 2, there is shown a block diagram of circuitry for providing the desired output signal. Gate 96 is illustrated as receiving the input current from a "95" generator as well as the program rate current. The rate "95" current, or equivalent control signal, is generated by the output of flip-flop 50, to maintain the pacemaker rate at 95 bpm (or any other selected value) while the program is being inputted to the pacemaker. The program rate current is, of course, the output of the current generators as illustrated in FIG. 1. The gate 96 is switched by the rate "95" signal. Under normal conditions, the program rate current is gated through circuit 96, and controls the stimulus generator 97 to generate signals at the programmed rate. Of course, for a demand pacemaker, the output is inhibited whenever a natural QRS is detected. When the magnet is applied and the rate "95" signal is inputted to gate 96, then a separate current generator "95" is gated through 96, so that stimulus generator 97 is controlled to operate at 97 bpm, in accordance with standard circuit techniques. At the same time, marker generator 90, which is triggered as discussed in connection with the operation of the circuit of FIG. 1, produces an output marker pulse which is gated through output circuit 98 to electrode E. Circuit 98 suitably contains standard circuitry for establishing the pulse width and pulse height.

The stimulus signals delivered to electrode E from the pacemaker are controlled by the inputted program data under normal circumstances, but are controlled at a rate of 95 bpm, or other selected rate, as long as a programming operation is on-going. This is illustrated in the second line of FIG. 3, which indicates that as soon as the magnet is first applied the pacer switches to 95 bpm on demand operation. The output signal returns to the programmed rate 3 beats following removal of the magnet, due to the operation of register 108, gate 110 and flip-flop 50. The third curve of FIG. 3 illustrates the positioning of the marker pulses following the fourth consecutive oscillator pulse while the magnet is applied.

There is thus disclosed a pacemaker system which is adapted to receive simple magnetic signals as generated by a hand held magnet, the system being adapted to receive and accept a first series of pulses which represents the decades (or tens) count of the dashed stimulus rate, and then a second series of pulses which represents the desired units count of the stimulus rate. The doctor simply counts the number of times that he or she applies the magnet until the proper decade count has been reached, and then holds the magnet applied for more than 4 internal pacemaker timing cycles, and looks for the marker pulse. He then applies the magnet again for a number of times corresponding to the desired units count of the programmed rate. Since, during the programming procedure, the pacemaker is operating at a fixed rate of 97 bpm, the doctor can easily time the application of the magnet so that it is within the constraints established in order that the pacemaker accept the applied signals. The "key" that is entered, in order that the pacemaker know that a proper program signal is being received (as opposed to spurious extraneous signals) is actually part of the program signal itself, such that the doctor does not have to think in terms of entering a separate key. The doctor applies the magnet in a simple direct decimal way which enables him to directly count the programmed heart rate as he or she is entering it. The marker pulses confirm that the new data has been properly entered.

We claim:

1. A pacemaker having a stimulus generator for delivering stimulus signals at a given rate, the rate of said stimulus signals being programmable, having means for receiving external program signals comprising on-off type signals and means for varying said rate as a function of said received program signals, characterized by said varying means comprising
   means for counting first and second sequenced series of said program signals;
   decade control means for controlling said rate so that the decade component of said rate corresponds to a first count of said counting means; and
   unit control means for controlling said rate so that the unit component of said rate corresponds to the other count of said counting means.

2. The pacemaker as described in claim 1, comprising means for enabling said unit control means only after said decade control means has controlled said decade component corresponding to said first count.

3. The pacemaker as described in claim 1, wherein said signals are on-off magnetic signals, and said controlling means controls said rate so that the decade component equals said first count.

4. The pacemaker as described in claim 3, wherein said controlling means controls said rate only when the off portion of each said magnetic signal has a time period less than a predetermined number of said stimulus signals.

5. The pacemaker as described in claim 4, comprising means for determining the time relationship of said program signals with said stimulus signals, and enabling said varying means only upon determining that such time relationship is within predetermined limits.

6. The pacemaker as described in claim 1, comprising means for controlling said stimulus generator to operate at a fixed rate while programming signals are being received.

7. The pacemaker as described in claim 1, wherein the count of said first series equals the decade component of the programmed stimulus rate.

8. The pacemaker as described in claim 1, wherein the count of said second series equals the units component of said programmed rate.

9. The pacemaker as described in claim 1, comprising marker means for generating a marker signal following rate programming of said pacemaker in accordance with said first count.

10. The pacemaker as described in claim 1, comprising marker means for generating a marker signal following rate programming of said pacemaker with each of said series of signals.

11. The pacemaker as described in claim 1, comprising means for limiting the programmed decade component to a predetermined range of numbers.

12. The pacemaker as described in claim 1, wherein said programming signals are generated by applying a magnet in the vicinity of the pacemaker, and said pacemaker comprises means for turning off the varying means when the magnet is removed for a time period corresponding to the three output pulses from the stimulus generator.

13. The pacemaker as described in claim 1, wherein said varying means comprises means for detecting a predetermined series of said program signals which constitute a key, and means for enabling said controlling means only upon detection of said key.

14. The pacemaker as described in claim 13, wherein said predetermined series is part of said first series.

15. A programmable cardiac pacemaker for generation of output signals suitable for delivery to a patient's heart, having receiving means for receiving externally generated program signals and signal generating circuitry for generating said output signals, said signal generating circuitry continuously providing timing signals representative of the timing of said circuitry, characterized by:
   program means for generating control signals as a function of the time relationship of said received program signals and said timing signals, means controlled by said control signals for distinguishing first and second sequenced groups of said program signals having a predetermined time relationship and obtaining first and second counts of same; and
   means for controlling the rate of generating said output signals so that the decades component of said rate in bpm corresponds to one of said counts and the unit component of said rate corresponds to the other of said counts.

16. The pacemaker as described in claim 12, comprising key means for decoding said first group of signals to produce an enabling key when said first group is determined to meet predetermined conditions, and means for enabling said control means only upon detecting said key.

17. A method for programming a cardiac pacing system, said system being adapted for generating of pacing signals suitable for delivery to a patient's heart, and having receiving means for receiving externally generated program signals and signal generating circuitry for generating said output signals at a rate corresponding to said received program signals, comprising:
   a. applying a first series of magnetic pulses in the vicinity of said pacemaker;
   b. detecting said first series of pulses and obtaining a count of said first series;
   c. applying a magnetic signal of predetermined form and enabling thereby storage of said first count;
   d. controlling the rate of said pacing signals in response to said enabling so that the decade component of said pacing signal rate in bpm corresponds to said first count; and
   e. if the unit component of said rate is not zero, applying a second group of magnetic signals, detecting and counting said second group of signals, enabling acceptance of said second group of signals by applying a magnetic signal of predetermined form, and further controlling the rate of said pacing signals so that the unit component of said rate in bpm corresponds to said second count.

18. The method as described in claim 17, wherein said applying comprises applying a hand held magnet.

* * * * *

UNITED STATES PATENT AND TRADEMARK OFFICE
CERTIFICATE OF CORRECTION

PATENT NO. : 4,388,929
DATED      : June 21, 1983
INVENTOR(S): Renirie et al.

It is certified that error appears in the above-identified patent and that said Letters Patent are hereby corrected as shown below:

Column 9, line 3, delete "97" and insert therefor -- 95 --.

Signed and Sealed this

Thirtieth Day of August 1983

[SEAL]

Attest:

GERALD J. MOSSINGHOFF

*Attesting Officer*    *Commissioner of Patents and Trademarks*